(12) United States Patent
Ratni

(10) Patent No.: US 11,370,802 B2
(45) Date of Patent: Jun. 28, 2022

(54) TRIAZOLO-AZEPINE DERIVATIVES

(71) Applicant: Hoffmann-La Roche Inc., Little Falls, NJ (US)

(72) Inventor: Hasane Ratni, Habsheim (FR)

(73) Assignee: Hoffmann-La Roche, Inc., Little Falls, NJ (US)

( * ) Notice: Subject to any disclaimer, the term of this patent is extended or adjusted under 35 U.S.C. 154(b) by 57 days.

(21) Appl. No.: 16/963,398

(22) PCT Filed: Jan. 21, 2019

(86) PCT No.: PCT/EP2019/051307
§ 371 (c)(1),
(2) Date: Jul. 20, 2020

(87) PCT Pub. No.: WO2019/141832
PCT Pub. Date: Jul. 25, 2019

(65) Prior Publication Data
US 2021/0395270 A1     Dec. 23, 2021

(30) Foreign Application Priority Data
Jan. 22, 2018 (EP) ..................... 18152763

(51) Int. Cl.
*C07D 519/00* (2006.01)
(52) U.S. Cl.
CPC ................... *C07D 519/00* (2013.01)
(58) Field of Classification Search
CPC ..................... C07D 487/04; C07D 519/00
USPC ........................ 514/214.02; 546/73
See application file for complete search history.

(56) References Cited

U.S. PATENT DOCUMENTS

| 7,476,662 B2 * | 1/2009 | Janssens .................. A61P 7/10 |
| | | 514/214.02 |
| 8,703,763 B2 | 4/2014 | Baumann et al. |
| 2012/0225884 A1 | 9/2012 | Baumann et al. |

OTHER PUBLICATIONS

"International Preliminary Report on Patentability—PCT/EP2019/051307/" (Report dated: Jul. 28, 2020),:1-7 (Aug. 6, 2020).

"International Search Report—PCT/EP2019/051307":pp. 1-6 (dated Mar. 6, 2019).

* cited by examiner

*Primary Examiner* — Kahsay Habte
(74) *Attorney, Agent, or Firm* — Genentech, Inc.; Richard G. A. Bone

(57) ABSTRACT

The present invention relates to a compound of formula (I) wherein Ar is (II) or (II); R is $CH_3$ or $OCH_3$; or a pharmaceutically acceptable acid addition salt or a corresponding enantiomer thereof. The compounds are modulators of γ-secretase (A β42) and may be useful for the treatment of Alzheimer's disease, cerebral amyloid angiopathy, hereditary cerebral hemorrhage with amyloidosis-Dutch type (HCHWA-D), multi-infarct dementia, dementia pugilistica or Down syndrome.

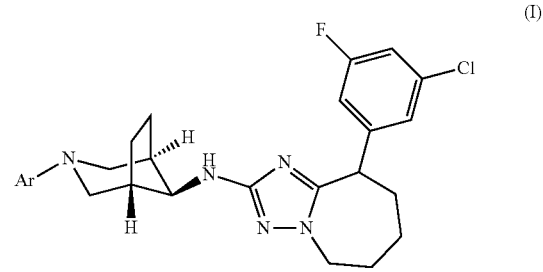

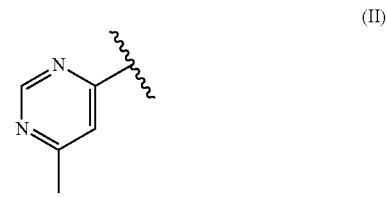

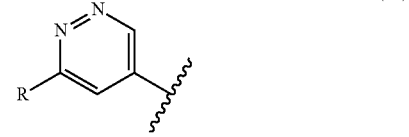

11 Claims, No Drawings

TRIAZOLO-AZEPINE DERIVATIVES

FIELD OF THE INVENTION

The present invention relates to pyrimidine derivatives useful as γ-secretase modulators, their manufacture, pharmaceutical compositions comprising said compounds and their use as medicaments for the treatment of diseases associated with the deposition of β-amyloid in the brain, such as Alzheimer's disease, cerebral amyloid angiopathy, hereditary cerebral hemorrhage with amyloidosis-Dutch type (HCHWA-D), multi-infarct dementia, dementia pugilistica and Down syndrome.

BACKGROUND OF THE INVENTION

Alzheimer's disease (AD) is the most common cause of dementia in later life. Pathologically, AD is characterized by the deposition of amyloid in extracellular plaques and intracellular neurofibrillary tangles in the brain. The amyloid plaques are mainly composed of amyloid peptides (Aβ peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Aβ peptides are derived from the same domain of the APP.

Aβ peptides are produced from APP through the sequential action of two proteolytic enzymes termed β- and γ-secretase. β-Secretase cleaves first in the extracellular domain of APP just outside of the trans-membrane domain (TM) to produce a C-terminal fragment of APP (CTFβ) containing the TM- and cytoplasmatic domain. CTFβ is the substrate for γ-secretase which cleaves at several adjacent positions within the TM to produce the Aβ peptides and the cytoplasmic fragment. Various proteolytic cleavages mediated by γ-secretase result in Aβ peptides of different chain length, e.g. Aβ38, Aβ40 and Aβ42. The latter one is regarded to be the more pathogenic amyloid peptide because of its strong tendency to form neurotoxic aggregates.

The β-secretase is a typical aspartyl protease. The γ-secretase is a high molecular weight complex that consists of four essential subunits: Presenilin (PS, including PS1 and PS2), nicastrin, anterior pharynx defective 1 (APH-1), and presenilin enhancer 2 (PEN-2). The atomic structure of human γ-secretase at 3.4 Å resolution has been published (X. Bai, C. Yan, G. Yang, P. Lu, D. Ma, L. Sun, R. Zhou, S. H. W. Scheres, Y. Shi, Nature 2015, 525, pages 212-217. The presenilins are bearing the catalytic site and represent a group of atypical aspartyl proteases which cleave their substrates within the TM of and which are themselves polytopic membrane proteins. The other essential components of γ-secretase, nicastrin and the products of the aph1 and pen-2 genes are believed to be responsible for substrate recognition and recruitment. Proven substrates for γ-secretase are APP and the proteins of the Notch receptor family, however, γ-secretase has a loose substrate specificity and many further membrane proteins unrelated to APP and Notch have been reported to be cleaved by the γ-secretase in vitro.

The γ-secretase activity is absolutely required for the production of Aβ peptides. This has been shown both by genetic means, i.e., ablation of the presenilin genes and by low-molecular-weight inhibitory compounds. According to the amyloid cascade hypothesis for AD the production and deposition of Aβ is the ultimate cause for the disease.

Therefore, it was believed that selective and potent inhibition of γ-secretase might be useful for the prevention and treatment of AD.

An alternative mode of treatment is the modulation of the γ-secretase activity which results in a selective reduction of the Aβ42 production. This will lead in an increase of shorter Aβ isoforms, such as Aβ38, Aβ37 or others, which have no or reduced capability for aggregation and plaque formation, and are not or less neurotoxic. Compounds which show this effect on modulating γ-secretase activity include certain non-steroidal anti-inflammatory drugs (NSAIDs) and related analogues (Weggen et al., Nature, 414 (2001) 212-16).

Thus, the compounds of this invention will be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis-Dutch type (HCHWA-D), multi-infarct dementia, dementia pugilistica and Down syndrome.

Numerous documents describe the current knowledge on γ-secretase modulation, for example the following publications:
Morihara et al, J. Neurochem., 83 (2002) 1009-12
Jantzen et al, J. Neuroscience, 22 (2002) 226-54
Takahashi et al, J. Biol. Chem., 278 (2003) 18644-70
Beher et al, J. Biol. Chem. 279 (2004) 43419-26
Lleo et al, Nature Med. 10 (2004) 1065-6
Kukar et al, Nature Med. 11 (2005) 545-50
Perretto et al, J. Med. Chem. 48 (2005) 5705-20
Clarke et al, J. Biol. Chem. 281 (2006) 31279-89
Stock et al, Bioorg. Med. Chem. Lett. 16 (2006) 2219-2223
Narlawar et al, J. Med. Chem. 49 (2006) 7588-91
Ebke et al, J. Biol. Chem., 286 (2011) 37181-86
Oehlich, Gijsen et al, J. Med. Chem., 54 (2011), 669-698
Li et al., Biochemistry, 52, (2013), 3197-3216
Hall et al, Progress in Med. Chem., 53 (2014) 101-145
Bursavich et al, J. Med. Chem., 59 (2016).

Therefore, modulating the γ-secretase activity is a promising therapeutic strategy for the treatment or prevention of diseases associated with the deposition of β-amyloid in the brain, such as Alzheimer's disease, cerebral amyloid angiopathy, hereditary cerebral hemorrhage with amyloidosis-Dutch type (HCHWA-D), multi-infarct dementia, dementia pugilistica and Down syndrome.

There is a need for new compounds, formulations, treatments and therapies to treat diseases and disorders associated with the deposition of β-amyloid in the brain. It is, therefore, an object of this invention to provide compounds useful for the treatment or prevention of such diseases and disorders with improved therapeutic properties.

SUMMARY OF THE INVENTION

In one aspect, the present invention relates to a compound of formula I,

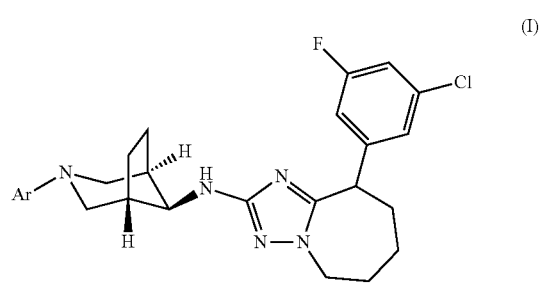

(I)

wherein
Ar is

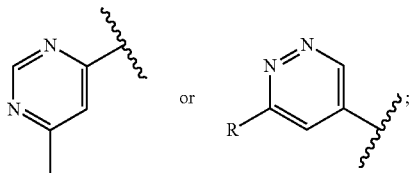

and
R is CH₃ or OCH₃;
or to a pharmaceutically acceptable acid addition salt or a corresponding enantiomer thereof.

In a further aspect, the present invention provides a process for preparing a compound of formula I as defined herein, which process comprises
a) reacting a compound of formula 2

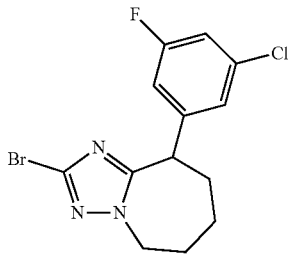

2 with a compound of formula 3

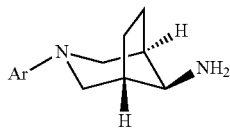

3 to a compound of formula I

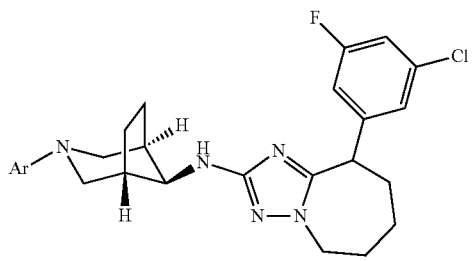

I wherein Ar has the meaning as defined herein, and, if desired, converting the compound obtained into a pharmaceutically acceptable acid addition salt, and
b) optionally separating a racemic compound of formula I by a chiral HPLC separation to a compound of formulas IA-1, IA-2, IB-1, IB-2, IB-3 and IB-4.

In a further aspect, the present invention provides a compound of formula I as described herein, whenever prepared by a process as described above.

In a further aspect, the present invention provides a medicament containing one or more compounds of formula (I) as described above and pharmaceutically acceptable excipients.

In a further aspect, the present invention provides the use of a compound as described herein for the manufacture of medicaments for the treatment of Alzheimer's disease, cerebral amyloid angiopathy, hereditary cerebral hemorrhage with amyloidosis-Dutch type (HCHWA-D), multi-infarct dementia, dementia pugilistica or Down syndrome.

In a further aspect, the present invention provides a compound of formula I as described herein, for use as a therapeutically active substance.

In a further aspect, the present invention provides the use of a compound of formula I as described herein for the treatment of Alzheimer's disease, cerebral amyloid angiopathy, hereditary cerebral hemorrhage with amyloidosis-Dutch type (HCHWA-D), multi-infarct dementia, dementia pugilistica or Down syndrome.

In a further aspect, the present invention provides a compound of formula I as described herein for use in the treatment of Alzheimer's disease, cerebral amyloid angiopathy, hereditary cerebral hemorrhage with amyloidosis-Dutch-type, multi-infarct dementia, dementia pugilistica or Down syndrome.

In a further aspect, the present invention provides a method for the treatment of Alzheimer's disease, cerebral amyloid angiopathy, hereditary cerebral hemorrhage with amyloidosis-Dutch type (HCHWA-D), multi-infarct dementia, dementia pugilistica or Down syndrome, which method comprises administering an effective amount of a compound of formula I as defined herein.

Now it has been found that the present compounds of formula I are modulators of γ-secretase, they may be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis-Dutch type (HCHWA-D), multi-infarct dementia, dementia pugilistica and Down syndrome.

DETAILED DESCRIPTION OF THE INVENTION

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Compounds of the Invention

In a first aspect, the present invention provides a compound of formula I

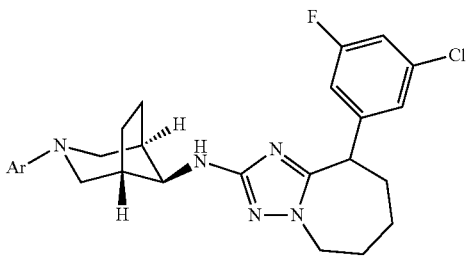

I wherein
Ar is

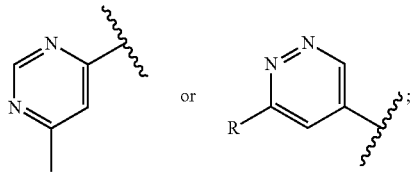

R is CH₃ or OCH₃;
or a pharmaceutically acceptable acid addition salt or a corresponding enantiomer thereof.

In one embodiment, there is provided compounds of formula IA-1 or IA-2,

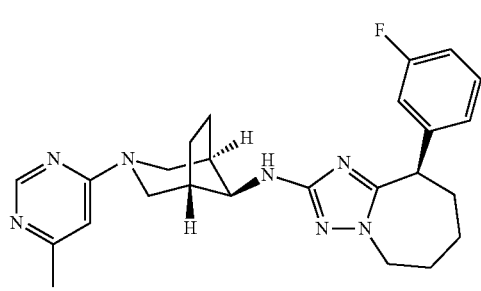

or a pharmaceutically acceptable acid addition salt thereof, which are the following compounds: (9R)-9-(3-chloro-5-fluoro-phenyl)-N-[(1S,5R,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine; or (9S)-9-(3-chloro-5-fluoro-phenyl)-N-[(1S,5R,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine; or a pharmaceutically acceptable acid addition salt thereof.

In one embodiment, there is provided the compounds of formulas IB-1, IB-2, IB-3 and IB-4

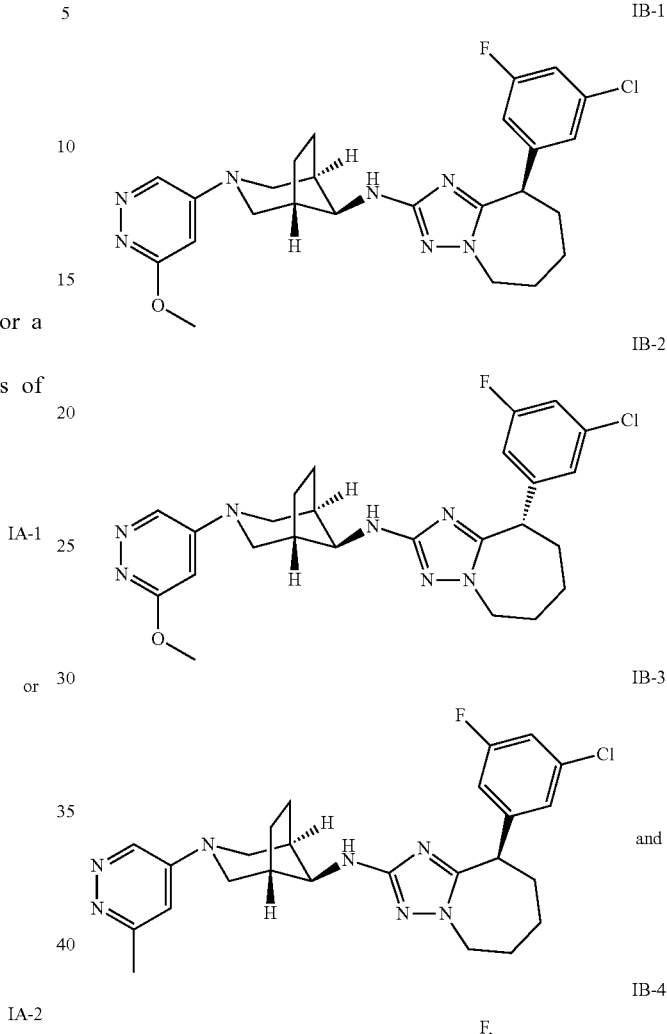

or a pharmaceutically acceptable acid addition salt thereof, which are the following compounds: (9R)-9-(3-chloro-5-fluoro-phenyl)-N-[(1S,5R,8S)-3-(6-methoxypyridazin-4-yl)-3-azabicyclo[3.2.1]octan-8-yl]-6,7,8,9-tetrahydro-5H-[1,2,4]triazolo[1,5-a]azepin-2-amine; (9S)-9-(3-chloro-5-fluoro-phenyl)-N-[(1S,5R,8S)-3-(6-methoxypyridazin-4-yl)-3-azabicyclo[3.2.1]octan-8-yl]-6,7,8,9-tetrahydro-5H-[1,2,4]triazolo[1,5-a]azepin-2-amine; (9R)-9-(3-chloro-5-fluoro-phenyl)-N-[(1S,5R,8S)-3-(6-methylpyridazin-4-yl)-3-azabicyclo[3.2.1]octan-8-yl]-6,7,8,9-tetrahydro-5H-[1,2,4]triazolo[1,5-a]azepin-2-amine; or (9S)-9-(3-chloro-5-fluoro-phenyl)-N-[(1S,5R,8S)-3-(6-methylpyridazin-4-yl)-3-azabicyclo[3.2.1]octan-8-yl]-6,7,8,9-tetrahydro-5H-[1,2, 4]triazolo[1,5-a]azepin-2-amine; or a pharmaceutically acceptable acid addition salt thereof.

Processes of Manufacturing

Processes for the manufacture of compounds of formula I as described herein are also an object of the present invention.

The present compounds of formula I and their pharmaceutically acceptable salts can be prepared by methods known in the art, for example, by a process described below, which process comprises a) reacting a compound of formula 2

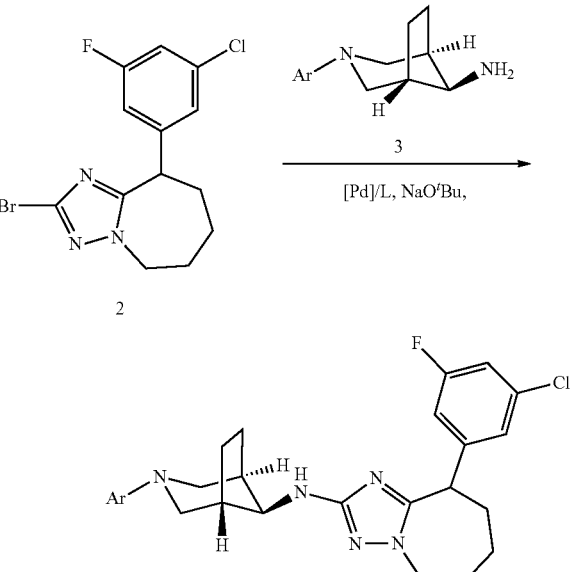

2 with a compound of formula 3

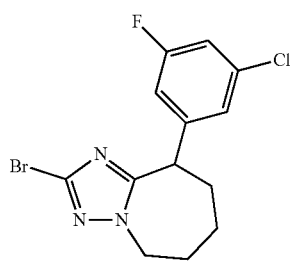

3 to a compound of formula I

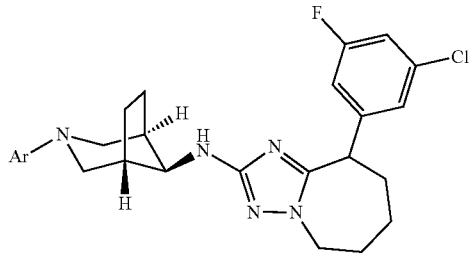

I wherein Ar have the meaning as described above, and, if desired, converting the compounds obtained into pharmaceutically acceptable acid addition salts, and b) optionally separating a racemic compound of formula I by a chiral HPLC separation to an enantiomer of formulas IA-1, IA-2, IB-1, IB-2, IB-3 and IB-4.

In one embodiment, compounds of formula I and their intermediates may be prepared by schemes 1 and 2 and by the description of 6 specific examples.

General Synthesis of Derivatives of Formula I

Scheme 1

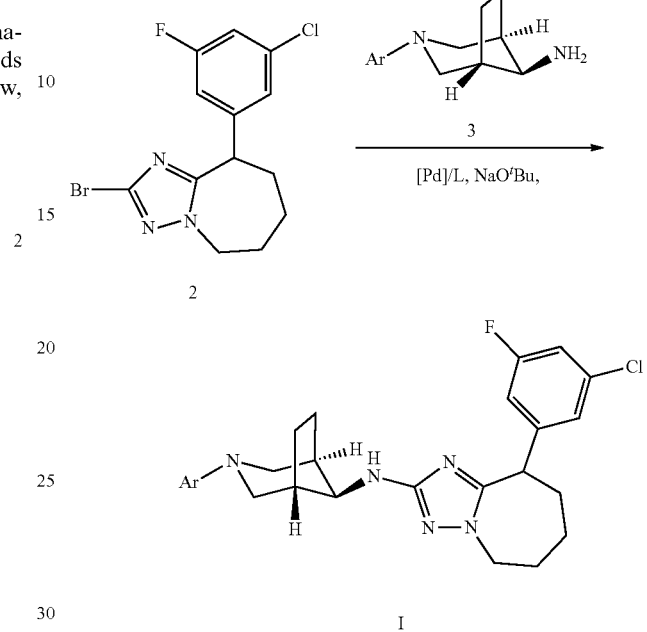

The preparation of derivatives of general formula I can be made via a Buchwald type cross coupling between a derivative of formula 2 and amino derivative of general formula 3 in the presence of a palladium catalyst (e.g. dibromo-bis-(tritert-butyl)-phosphine-palladium, CAS185812-86-6) or tri(dibenzylidenacetonne) dipalladium(0), CAS51364-51-3) in the presence of a ligand (e.g. 2-di-tert-butylphosphino-2',4',6'-triisopropylbiphenyl, CAS564483-19-8) and a base (e.g. NaOtBu).

General Synthesis of Intermediates 3

Scheme 2

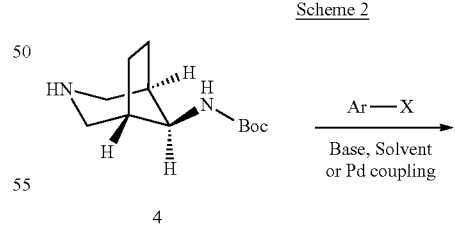

4

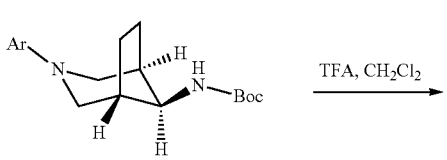

5

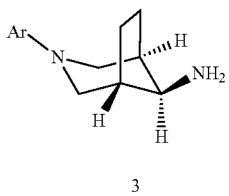

3

Compounds of formula 3 used in scheme 1 can be prepared according to scheme 2, starting from tert-butyl N-[(1S,5R,8S)-3-azabicyclo[3.2.1]octan-8-yl]carbamate 4 (CAS 847862-26-4). The coupling of 4 with heterocyclic halides of general formula Ar—X can be accomplished under thermal conditions in a solvent such as ethanol or NMP in the presence of a base such as Et₃N or by using displacement reactions under catalytic conditions (like e.g. palladium(0) or copper(II) catalysis) to provide compounds of formula 5. After deprotection with acid e.g. trifluoroacetic acid compounds of formula 3 were obtained.

The heterocycles halides of formula Ar—X are either commercially available or known in the literature, so they can be prepared by methods known in the art.

Medicaments and Administration

Another object of the present invention is a medicament comprising one or more compounds of formula I as described herein and at least one pharmaceutically acceptable excipient.

The compounds of formula I and the pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, parenterally, e.g. in the form of injection solutions. The administration can also be effected topically, e.g. transdermal administration, or in form of eye drops or ear drops.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the inhibition of Aβ42 secretion, such as of Alzheimer's disease.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The pharmaceutical compositions according to the invention may be prepared as follows.

Preparation of Pharmaceutical Compositions Comprising Compounds of the Invention Tablet Formulation (Wet Granulation)

| Item | Ingredients | mg/tablet | | | |
|---|---|---|---|---|---|
| | | 5 | 25 | 100 | 500 |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| Item | Ingredients | mg/capsule | | | |
|---|---|---|---|---|---|
| | | 5 | 25 | 100 | 500 |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

Indications

Also an object of the present invention is a compound of formula I as described herein for use as a therapeutically active substance.

In one aspect, the present invention provides the use of a compound of formula I as described herein for the manufacture of a medicament for the treatment of Alzheimer's disease, cerebral amyloid angiopathy, hereditary cerebral hemorrhage with amyloidosis-Dutch type (HCHWA-D), multi-infarct dementia, dementia pugilistica or Down syndrome.

In one embodiment, the present invention provides the use of a compound of formula I as described herein for the manufacture of a medicament for the treatment of Alzheimer's disease.

In a further aspect, the present invention provides a compound of formula I as described herein for use in the treatment of Alzheimer's disease, cerebral amyloid angiopathy, hereditary cerebral hemorrhage with amyloidosis-Dutch type (HCHWA-D), multi-infarct dementia, dementia pugilistica or Down syndrome.

In one embodiment, the present invention provides a compound of formula I as described herein for use in the treatment of Alzheimer's disease.

In a further aspect, the present invention provides the use of a compound of formula I as described herein for the treatment of Alzheimer's disease, cerebral amyloid angiopathy, hereditary cerebral hemorrhage with amyloidosis-Dutch type (HCHWA-D), multi-infarct dementia, dementia pugilistica or Down syndrome.

In one embodiment, the present invention provides the use of a compound of formula I as described herein for the treatment of Alzheimer's disease.

In a further aspect, the present invention provides a method for the treatment of Alzheimer's disease, cerebral amyloid angiopathy, hereditary cerebral hemorrhage with amyloidosis-Dutch type (HCHWA-D), multi-infarct dementia, dementia pugilistica or Down syndrome, which method comprises administering an effective amount of a compound of formula I as described herein.

In one embodiment, the present invention provides a method for the treatment of Alzheimer's disease, which method comprises administering an effective amount of a compound of formula I as described herein.

EXAMPLES

The following examples are provided for illustration of the invention. They should not be considered as limiting the scope of the invention, but merely as being representative thereof.

1) Preparative Examples 1.1) General
Analytical Methods:
a) HPLC (method LCMS_fastgradient)
Column: Agilent Zorbax Eclipse Plus C18, Rapid Resolution HT, 2.1×30 mm, 1.8 µm, Part. no. 959731-902
Solvent A: Water 0.01% Formic Acid; Solvent B: acetonitrile (MeCN)
Gradients:

| Time [min] | Flow Rate [ml/min] | % A | % B |
|---|---|---|---|
| Initial | 0.8 | 97 | 3 |
| 0.2 | 1.0 | 97 | 3 |
| 1.7 | 1.0 | 3 | 97 |
| 2.0 | 1.0 | 3 | 97 |
| 2.1 | 1.0 | 97 | 3 |

Abbreviations:
The following abbreviations were used in the experimental part:
tBuONa=sodium tert-butyloxide;
DMF=dimethylformamide;
EtOAc=ethyl acetate;
EtOH=ethanol;
Et₃N=triethylamine;
LDA=lithium diisopropylamide;
MeOH=methanol;
Me₂SO=dimethylsulfoxide;
RT=room temperature, 20-25° C.;
TFA=trifluoroacetic acid;
THF=tetrahydrofuran;
TBME=methyl-tert-butylether;
TLC=thin layer chromatography;
THP=tetrahydropyran.

1.2) Preparation of Intermediates

Preparation of Intermediate 2

2-Bromo-9-(3-chloro-5-fluoro-phenyl)-6,7,8,9-tetra-hydro-5H-[1,2,4]triazolo[1,5-a]azepine

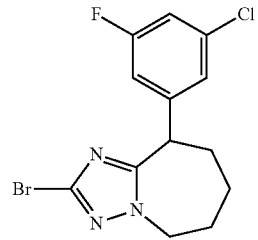 [SMILES: Fc1cc(Cl)cc(C2CCCCn3nc(Br)nc32)c1]

Step 1: Methyl 6-chloro-2-(3-chloro-5-fluoro-phenyl)hexanoate

To a cooled (−78° C.) solution of LDA (24.6 mmol) in THF (30 mL) was added dropwise over 30 minutes a THF (20 mL) solution of methyl 2-(3-chloro-5-fluoro-phenyl) acetate (4.75 g, 23.4 mmol). Stirring was continued for one more hour, before a THF (20 mL) solution of 1-chloro-4-iodobutane (5.12 g, 23.4 mmol) was added over 20 minutes, still at (−78° C. After two hours, the temperature was slowly raised to RT over an hour and stirring continued overnight. The reaction was quenched by addition of a saturated aqueous solution of NH$_4$Cl (100 mL) and the product extracted with TBME. The organic phase was dried over Na$_2$SO$_4$, concentrated under vacuo. A column chromatography (a gradient: TBME in heptane) gave methyl 6-chloro-2-(3-chloro-5-fluoro-phenyl)hexanoate (4.76 g, 69%) as a light yellow oil.

Step 2:
6-chloro-2-(3-chloro-5-fluoro-phenyl)hexanoic Acid

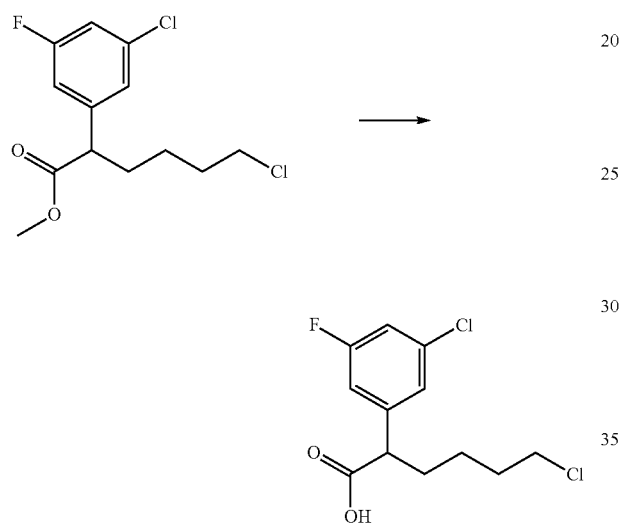

To a stirred solution of methyl 6-chloro-2-(3-chloro-5-fluoro-phenyl)hexanoate (4.75 g, 16.2 mmol) in THF (60 mL) at RT was added LiOH.H$_2$O (2.04 g, 48.6 mmol) in solution in H$_2$O (60 mL) and MeOH (6 mL). Stirring was continued overnight at RT. An aqueous solution of HCl (2M, 50 mL) was added, resulting in a white precipitation. The product was extracted with EtOAc and the organic phase was washed with brine and dried over Na$_2$SO$_4$. After concentration and drying under vacuo, 6-chloro-2-(3-chloro-5-fluoro-phenyl)hexanoic acid (4.7 g, 99%) was obtained as a white solid. MS (ES+) m/z: 277.3 [(M−H)$^+$].

Step 3: 5-[5-chloro-1-(3-chloro-5-fluoro-phenyl)pentyl]-1H-1,2,4-triazol-3-amine

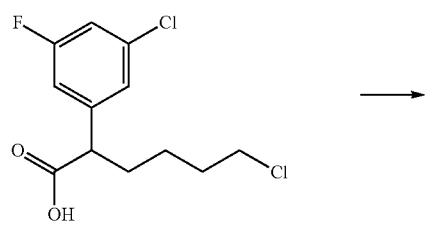

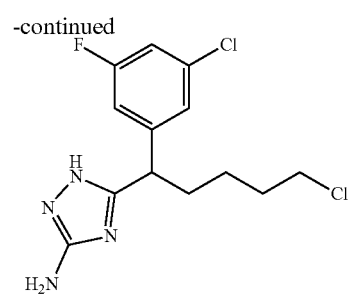

To a stirred solution of 6-chloro-2-(3-chloro-5-fluoro-phenyl)hexanoic acid (2.1 g, 7.5 mmol) in toluene (20 mL) was added thionyl chloride (2.09 mL, 28.8 mmol) and the reaction heated at 90° C. for 3 hours and then overnight at RT. The reaction was concentrated under vacuo to dryness giving a light yellow oil. To this residue was added hydrazinecarboximidamide hydrochloride (1.66 g, 15 mmol). The resulting thick brown paste was stirred at 140° C. for 45 minutes and cool down to RT. H$_2$O (30 mL) and K$_2$CO$_3$ (1.50 g, 10.9 mmol) were added and heating was continued at 110° C. for 20 minutes, cooled down to RT before the pH was adjusted to pH=7 with addition of acetic acid. The product was extracted with CH$_2$Cl$_2$ and the organic phase dried over Na$_2$SO$_4$ and concentrated under vacuo giving 5-[5-chloro-1-(3-chloro-5-fluoro-phenyl)pentyl]-1H-1,2,4-triazol-3-amine (1.96 g, 82%) as a beige solid. MS (ES+) m/z: 317.2 [(M+H)$^+$].

Step 4: 9-(3-chloro-5-fluoro-phenyl)-6,7,8,9-tetrahydro-5H-[1,2,4]triazolo[1,5-a]azepin-2-amine

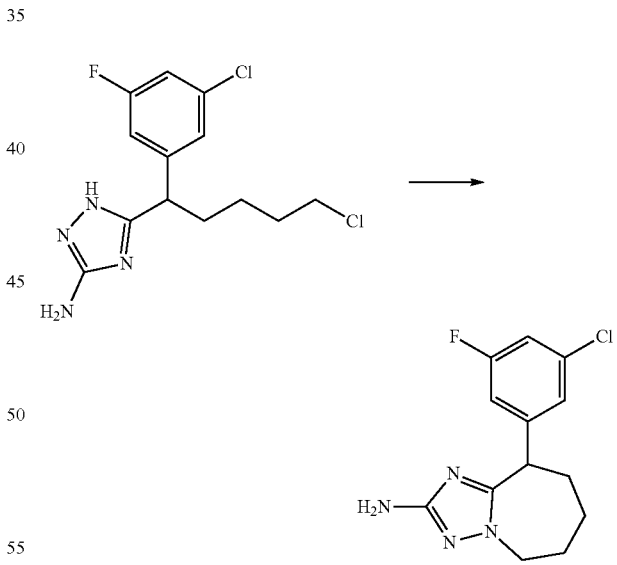

To a solution of 5-[5-chloro-1-(3-chloro-5-fluoro-phenyl)pentyl]-1H-1,2,4-triazol-3-amine (1.96 g, 6.18 mmol) in DMF (15 mL) was added tBuONa (0.65 g, 6.8 mmol) and LiCl (0.29 g, 6.8 mmol). The reaction mixture was then heated at 85° C. for one hour, cooled down to RT and quenched by addition of H$_2$O (25 mL). The product was extracted with EtOAc several times, the combined organic phases dried over Na$_2$SO$_4$ and concentrated under vacuum. A column chromatography (NH$_3$/MeOH in CH$_2$Cl$_2$) gave 9-(3-chloro-5-fluoro-phenyl)-6,7,8,9-tetrahydro-5H-[1,2,4]

triazolo[1,5-a]azepin-2-amine (0.62 g, 35%) as a white solid. MS (ES+) m/z: 281.3 [(M+H)⁺].

Step 5: 2-bromo-9-(3-chloro-5-fluoro-phenyl)-6,7,8,9-tetrahydro-5H-[1,2,4]triazolo[1,5-a]azepine

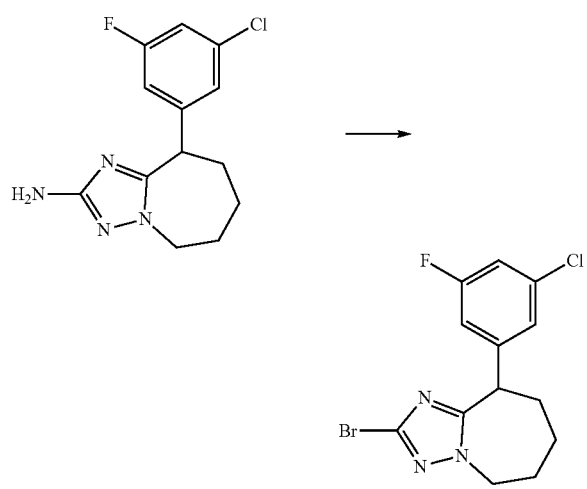

To 9-(3-chloro-5-fluoro-phenyl)-6,7,8,9-tetrahydro-5H-[1,2,4]triazolo[1,5-a]azepin-2-amine (0.36 g, 1.29 mmol) in CH₃CN (12 mL) was added CuBr₂ (0.43 g, 1.93 mmol) resulting in a dark green/brown solution. Tert-butyl nitrate (0.25 mL, 1.93 mmol) was then added in five portions over 15 minutes at RT. The reaction mixture was then heated at 65° C. for 30 minutes, cooled down to RT and quenched by addition of H₂O (8 mL). The product was extracted with EtOAc, and the combined organic phases washed successively with H₂O, an aqueous NH₄OH solution (25%, 10 mL) and then brine. The organic phase was dried over Na₂SO₄, concentrated under vacuo and a column chromatography (gradient: EtOAc in heptane) gave 2-bromo-9-(3-chloro-5-fluoro-phenyl)-6,7,8,9-tetrahydro-5H-[1,2,4]triazolo[1,5-a]azepine (0.42 g, 95%) as a white solid. MS (ES+) m/z: 344.1; 346.1 [(M+H)⁺].

Preparation of Intermediates of Type 3

Intermediate 3-1

(1R,5S,8S)-3-(6-methylpyrimidin-4-yl)-3-azabicyclo[3.2.1]octan-8-amine

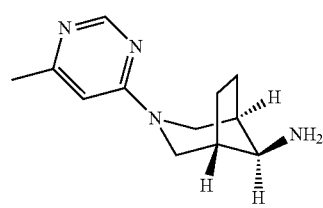 [SMILES: Cc1cc(N2C[C@H]3CC[C@@H](C2)[C@@H]3N)ncn1]

Step 1

In a sealed tube tert-butyl N-[(1R,5S,8S)-3-azabicyclo[3.2.1]octan-8-yl]carbamate (500 mg, 2.21 mmol) was dissolved in EtOH (10 mL) and 4-chloro-6-methylpyrimidine (869 mg, 6.63 mmol) was added followed by triethylamine (894 mg, 1.23 mL, 8.84 mmol). The reaction mixture was stirred at 130° C. overnight. The crude reaction mixture was concentrated in vacuum. The residue was diluted with 20 mL of CH₂Cl₂ and 20 mL of water. The organic phase was extracted with CH₂Cl₂ (3×20 mL), dried over MgSO₄ and concentrated in vacuum. The crude material was purified by flash chromatography (0% to 100% EtOAc in heptane) to afford tert-butyl N-[(1R,5S,8S)-3-(6-methylpyrimidin-4-yl)-3-azabicyclo[3.2.1]octan-8-yl]carbamate as a yellow solid (496 mg, 71% yield). MS (ES+) m/z: 319.2 [(M+H)⁺]

Step 2

To a light yellow solution of tert-butyl N-[(1R,5S,8S)-3-(6-methylpyrimidin-4-yl)-3-azabicyclo[3.2.1]octan-8-yl]carbamate (260 mg, 817 µmol) in CH₂Cl₂ (8 mL) was added TFA (931 mg, 629 µl, 8.17 mmol). The reaction mixture was stirred at room temperature overnight and concentrated in vacuum. The crude material was purified by Ion-exchange column (Si—SCX-2, 10 g, washed with MeOH and liberated with MeOH (NH₃ 2M)) to afford (1R,5S,8S)-3-(6-methylpyrimidin-4-yl)-3-azabicyclo[3.2.1]octan-8-amine 3-1 (195 mg, 804 µmol, 98.5% yield) that was used in the next step without further purification. MS (ES+) m/z: 219.2 [(M+H)⁺]

Intermediate 3-2

(1R,5S,8S)-3-(6-methoxypyridazin-4-yl)-3-azabicyclo[3.2.1]octan-8-amine

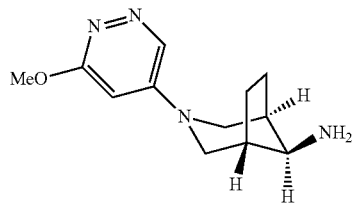 [SMILES: COc1cc(N2C[C@H]3CC[C@@H](C2)[C@@H]3N)cnn1]

Step 1

In analogy to the preparation of the intermediate 3-1 (step 1) from tert-butyl N-[(1R,5S,8S)-3-azabicyclo[3.2.1]octan-8-yl]carbamate (2.00 g, 8.84 mmol) and 3,5-dichloropyridazine (2.0 g, 13.4 mmol) in a sealed tube at 90° C. using EtOH as solvent in the presence of Et₃N (3.63 g, 5.0 mL, 35.9 mmol), tert-butyl N-[(1R,5S,8S)-3-(6-chloropyridazin-4-yl)-3-azabicyclo[3.2.1]octan-8-yl]carbamate (1.71 g, 54%) was obtained as a white solid. MS (ES+) m/z: 339.2 [(M+H)⁺].

Step 2

To a solution of tert-butyl N-[(1R,5S,8S)-3-(6-chloropyridazin-4-yl)-3-azabicyclo[3.2.1] octan-8-yl]carbamate (963 mg, 2.70 mmol) in MeOH (22 mL) in a sealed tube was added a methanol solution of NaOMe (25%, 1.9 mL, 8.3 mmol). The reaction mixture was heated at 85° C. overnight. The reaction mixture was adsorbed on Isolute HM-N and a column chromatography gave tert-butyl N-[(1R,5S,8S)-3-

(6-methoxypyridazin-4-yl)-3-azabicyclo[3.2.1] octan-8-yl]carbamate (362 mg, 38%) as a white solid. MS (ES+) m/z: 335.2 [(M+H)+].

Step 3

In analogy to the preparation of intermediate 3-1 (step 2) from tert-butyl N-[(1R,5S,8S)-3-(6-methoxypyridazin-4-yl)-3-azabicyclo[3.2.1]octan-8-yl]carbamate (0.93 g, 2.72 mmol) in $CH_2Cl_2$ in the presence of TFA (1.12 g, 0.76 mL, 9.86 mmol), (1R,5S,8S)-3-(6-methoxypyridazin-4-yl)-3-azabicyclo[3.2.1]octan-8-amine (225 mg, 96%) was obtained as a white solid and used directly in the next step without further purification. MS (ES+) m/z: 235.2 [(M+H)+].

Intermediate 3-3

(1R,5S,8S)-3-(6-methylpyridazin-4-yl)-3-azabicyclo[3.2.1]octan-8-amine

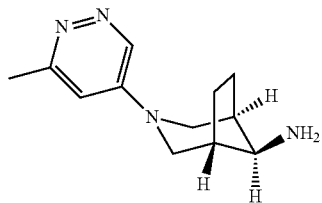 [SMILES: Cc1cc(N2C[C@H]3CC[C@@H](C2)[C@@H]3N)cnn1]

Step 1

To a stirred solution of tert-butyl N-[(1R,5S,8S)-3-(6-chloropyridazin-4-yl)-3-azabicyclo[3.2.1]octan-8-yl]carbamate (0.84 g, 2.48 mmol, described herein above) in dioxane (50 mL), was added methylboronic acid (0.59 g, 9.92 mmol), 1,1'-bis(diphenylphosphino)ferrocene-palladium(II) dichloride. $CH_2Cl_2$ complex (0.20 g, 0.25 mmol), cesium carbonate (3.63 g, 11.2 mmol) and $H_2O$ (5.0 mL). The reaction mixture was heated at 85° C. for 48 hours and then another 1,1'-bis(diphenylphosphino)ferrocene-palladium(II) dichloride $CH_2Cl_2$ complex (0.20 g, 0.25 mmol) was added and 2,4,6-trimethyl-13,5,2,4,6-trioxatriborinane (0.94 g, 7.44 mmol). Stirring was continued further for 20 hours, cooled down to RT, diluted with EtOAc, filtered over Celite® ("diatomaceous earth") and concentrated under vacuo. A column chromatography gave tert-butyl N-[(1R, 5S,8S)-3-(6-methylpyridazin-4-yl)-3-azabicyclo[3.2.1]octan-8-yl]carbamate (0.15 g, 18%) as a light grey solid. MS (ES+) m/z: 319.3 [(M+H)+].

Step 2

In analogy to the preparation of intermediate 3-1 (step 2) from tert-butyl N-[(1R,5S,8S)-3-(6-methylpyridazin-4-yl)-3-azabicyclo[3.2.1]octan-8-yl]carbamate (0.14 g, 0.44 mmol) in $CH_2Cl_2$ in the presence of TFA, (1R,5S,8S)-3-(6-methylpyridazin-4-yl)-3-azabicyclo[3.2.1]octan-8-amine (90 mg, 95%) was obtained as a white solid and used directly in the next step without further purification. MS (ES+) m/z: 219.3 [(M+H)+].

1.3) General Procedure 1: Buchwald Coupling Reaction

To a solution of the derivative 2, in 1,4-dioxane was added 1.1 equivalent of an intermediate 3. The reaction mixture was degassed and a palladium catalyst [either dibromo-bis-(tritert-butyl)-phosphine-palladium (0.1 eq. CAS185812-86-6) or tri(dibenzylidenacetonne) dipalladium(0) (CAS51364-51-3) in the presence of 2-di-tert-butylphosphino-2',4',6'-triisopropylbiphenyl (CAS564483-19-8) and NaOtBu (2.1 eq) were added. The reaction mixture was heated at 100° C. until completion of the reaction (usually between 2 and 8 hours) and concentrated under vacuo. A purification was done either by column chromatography or reverse phase preparative HPLC to afford the desired product.

Examples 1 and 2

(9R)-9-(3-chloro-5-fluoro-phenyl)-N-[(1S,5R,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine and (9S)-9-(3-chloro-5-fluoro-phenyl)-N-[(1S,5R,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine

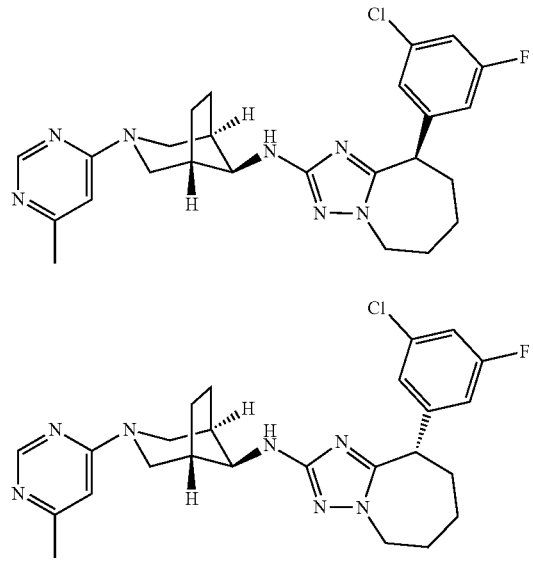

Using the general procedure of the Buchwald coupling between the intermediate (3.1) (1R,5S,8S)-3-(6-methylpyrimidin-4-yl)-3-azabicyclo[3.2.1]octan-8-amine and the compound 2-bromo-9-(3-chloro-5-fluoro-phenyl)-6,7,8,9-tetrahydro-5H-[1,2,4]triazolo[1,5-a]azepine (2) followed by a chiral HPLC separation of the enantiomers was prepared 13 mg of (9R)-9-(3-chloro-5-fluoro-phenyl)-N-[(1S,5R,8S)-

3-(6-methylpyrimidin-4-yl)-3-azabicyclo[3.2.1]octan-8-yl]-6,7,8,9-tetrahydro-5H-[1,2,4]triazolo[1,5-a]azepin-2-amine as a white solid (MS (ES+) m/z: 482.2 [(M+H)⁺]) and 13 mg of (9S)-9-(3-chloro-5-fluoro-phenyl)-N-[(1S,5R,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine as a white solid (MS (ES+) m/z: 482.2 [(M+H)⁺]).

Examples 3 and 4

(9R)-9-(3-chloro-5-fluoro-phenyl)-N-[(1S,5R,8S)-3-(6-methoxypyridazin-4-yl)-3-azabicyclo[3.2.1]octan-8-yl]-6,7,8,9-tetrahydro-5H-[1,2,4]triazolo[1,5-a]azepin-2-amine and (9S)-9-(3-chloro-5-fluoro-phenyl)-N-[(1S,5R,8S)-3-(6-methoxypyridazin-4-yl)-3-azabicyclo[3.2.1]octan-8-yl]-6,7,8,9-tetrahydro-5H-[1,2,4]triazolo[1,5-a]azepin-2-amine

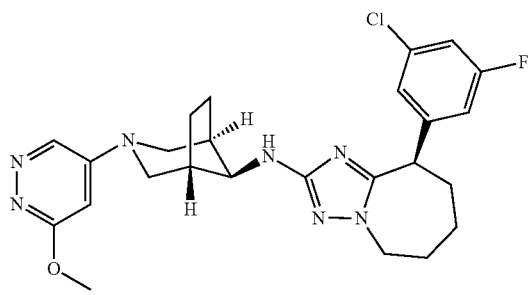

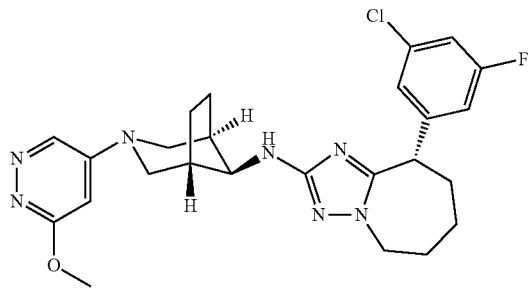

Using the general procedure of the Buchwald coupling between the intermediate (3.2) (1R,5S,8S)-3-(6-methoxypyridazin-4-yl)-3-azabicyclo[3.2.1]octan-8-amine and the compound 2-bromo-9-(3-chloro-5-fluoro-phenyl)-6,7,8,9-tetrahydro-5H-[1,2,4]triazolo[1,5-a]azepine (2) followed by a chiral HPLC separation of the enantiomers was prepared 33 mg of (9R)-9-(3-chloro-5-fluoro-phenyl)-N-[(1S,5R,8S)-3-(6-methoxypyridazin-4-yl)-3-azabicyclo[3.2.1]octan-8-yl]-6,7,8,9-tetrahydro-5H-[1,2,4]triazolo[1,5-a]azepin-2-amine as a white solid (MS (ES+) m/z: 498.3 [(M+H)⁺]) and 32 mg of (9S)-9-(3-chloro-5-fluoro-phenyl)-N-[(1S,5R,8S)-3-(6-methoxypyridazin-4-yl)-3-azabicyclo[3.2.1]octan-8-yl]-6,7,8,9-tetrahydro-5H-[1,2,4]triazolo[1,5-a]azepin-2-amine as a white solid (MS (ES+) m/z: 498.3 [(M+H)⁺]).

Examples 5 and 6

(9R)-9-(3-chloro-5-fluoro-phenyl)-N-[(1S,5R,8S)-3-(6-methylpyridazin-4-yl)-3-azabicyclo[3.2.1]octan-8-yl]-6,7,8,9-tetrahydro-5H-[1,2,4]triazolo[1,5-a]azepin-2-amine and (9S)-9-(3-chloro-5-fluoro-phenyl)-N-[(1S,5R,8S)-3-(6-methylpyridazin-4-yl)-3-azabicyclo[3.2.1]octan-8-yl]-6,7,8,9-tetrahydro-5H-[1,2,4]triazolo[1,5-a]azepin-2-amine

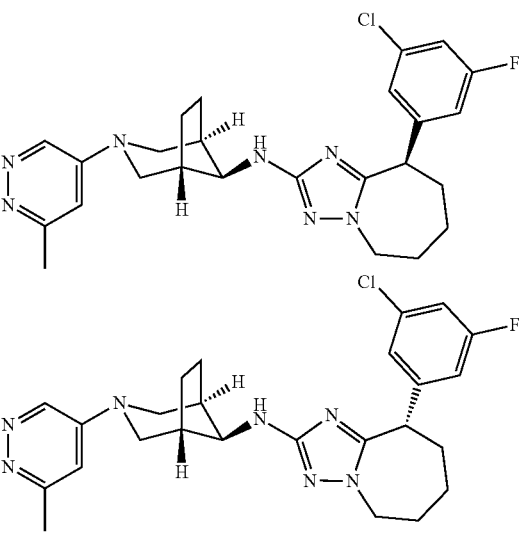

Using the general procedure of the Buchwald coupling between the intermediate (3.3) (1R,5S,8S)-3-(6-methylpyridazin-4-yl)-3-azabicyclo[3.2.1]octan-8-amine and the compound 2-bromo-9-(3-chloro-5-fluoro-phenyl)-6,7,8,9-tetrahydro-5H-[1,2,4]triazolo[1,5-a]azepine (2) followed by a chiral HPLC separation of the enantiomers was prepared 21 mg of (9R)-9-(3-chloro-5-fluoro-phenyl)-N-[(1S,5R,8S)-3-(6-methylpyridazin-4-yl)-3-azabicyclo[3.2.1]octan-8-yl]-6,7,8,9-tetrahydro-5H-[1,2,4]triazolo[1,5-a]azepin-2-amine as a white solid (MS (ES+) m/z: 482.3 [(M+H)⁺]) and 21 mg of (9S)-9-(3-chloro-5-fluoro-phenyl)-N-[(1S,5R,8S)-3-(6-methylpyridazin-4-yl)-3-azabicyclo[3.2.1]octan-8-yl]-6,7,8,9-tetrahydro-5H-[1,2,4]triazolo[1,5-a]azepin-2-amine as a white solid (MS (ES+) m/z: 482.3 [(M+H)⁺]).

2) Biological Examples 2.1) Assay Procedure: Cellular γ-Secretase Assay

The compounds were investigated in accordance with the test given hereinafter.

Human neuroglioma H4 cells overexpressing human APP695 with the Swedish double mutation (K595N/M596L) were plated at 30,000 cells/well/100 µl in 96-well plates in IMDM media containing 10% FCS, 0.2 mg/l Hygromycin B and incubated at 37° C., 5% Co₂.

3-4 hours post plating, compounds are diluted in media and 50 µl is added as 1.5-fold concentrate to achieve the final concentration. Compound incubation is performed for 24 hours. Final doses typically range from 4 µM down to 0.0013 µM in half-log steps resulting in an eight point dose response curve.

Appropriate controls using vehicle only and a reference compound were applied to this assay. The final concentration of Me$_2$SO was 0.4%.

After incubation at 37° C., 5% CO$_2$, the supernatant was subjected to quantification of secreted Aβ42 by the means of an AlphaLisa® assay kit (Human Amyloid beta 1-42, Perkin Elmer Inc.). 20 µl of the cell culture supernatant was transferred to an assay plate. Then 10 µl of a mixture of the AlphaLisa® coupled capture antibody and the biotinylated detection antibody was added and incubated for 3 hours at room temperature while softly shaking the assay plate. After a further addition of 20 µl of the Donor beads the assay plate was incubated for 30 min at room temperature and constant shaking without exposure to direct light. The assay plate was then read on a Paradigm AlphaLisa® Reader using the build-in program with excitation at 680 nm and emission at 570 nm.

The measured signals were then used to calculate IC$_{50}$ values for inhibition of Aβ42 secretion by nonlinear regression fit analysis using XLfit 5.3 software (from IDBS Ltd).

2.2) Results

The table below shows the data for all compounds for the inhibition of Aβ42 secretion:

| Example No. | Aβ42 IC$_{50}$ (uM) |
|---|---|
| 1 | 0.008 |
| 2 | 0.012 |
| 3 | 0.008 |
| 4 | 0.014 |
| 5 | 0.017 |
| 6 | 0.014 |

The invention claimed is:

1. A compound of formula I

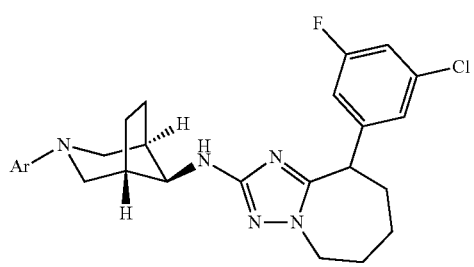

wherein:
Ar is

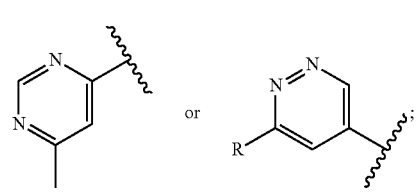

and
R is CH$_3$ or OCH$_3$;
or a pharmaceutically acceptable acid addition salt or a corresponding enantiomer thereof.

2. A compound of formula IA-1 or IA-2,

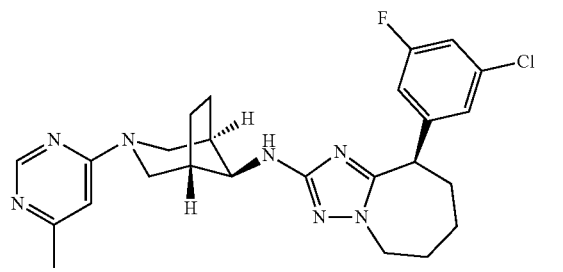

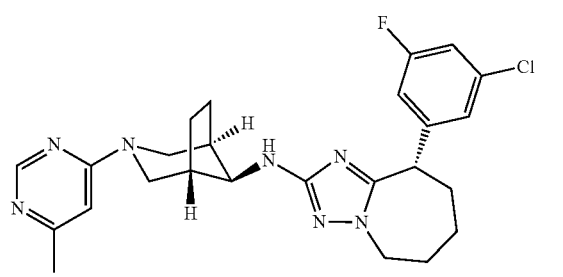

which have the following respective formulae:
(9R)-9-(3-chloro-5-fluoro-phenyl)-N-[(1S,5R,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine; and
(9S)-9-(3-chloro-5-fluoro-phenyl)-N-[(1S,5R,8S)-3-(6-methylpyrimidin-4-yl)-3-azabicyclo[3.2.1]octan-8-yl]-6,7,8,9-tetrahydro-5H-[1,2,4]triazolo[1,5-a]azepin-2-amine;
or a pharmaceutically acceptable acid addition salt thereof.

3. A compound of formula IB-1, IB-2, IB-3 or IB-4,

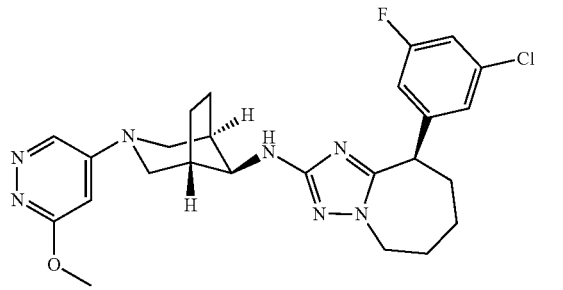

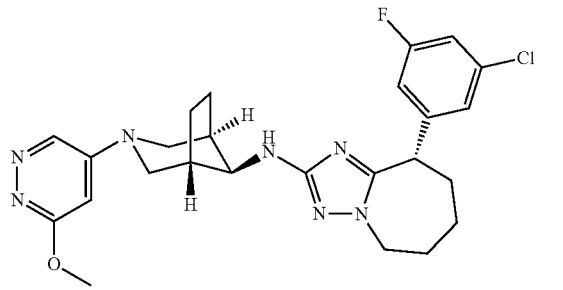

-continued

IB-3

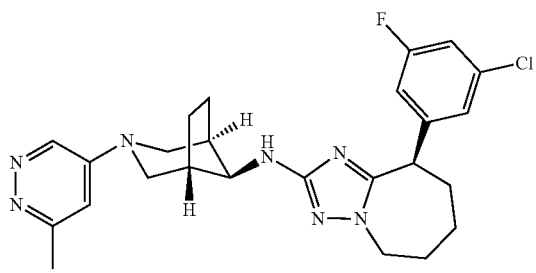

IB-4

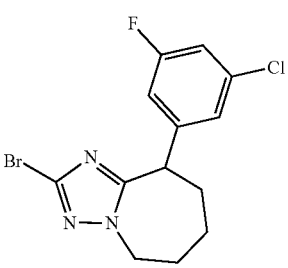

which have the following respective formulae:
- (9R)-9-(3-chloro-5-fluoro-phenyl)-N-[(1S,5R,8S)-3-(6-methoxypyridazin-4-yl)-3-azabicyclo[3.2.1]octan-8-yl]-6,7,8,9-tetrahydro-5H-[1,2,4]triazolo[1,5-a]azepin-2-amine; and
- (9S)-9-(3-chloro-5-fluoro-phenyl)-N-[(1S,5R,8S)-3-(6-methoxypyridazin-4-yl)-3-azabicyclo[3.2.1]octan-8-yl]-6,7,8,9-tetrahydro-5H-[1,2,4]triazolo[1,5-a]azepin-2-amine;
- (9R)-9-(3-chloro-5-fluoro-phenyl)-N-[(1S,5R,8S)-3-(6-methoxypyridazin-4-yl)-3-azabicyclo[3.2.1]octan-8-yl]-6,7,8,9-tetrahydro-5H-[1,2,4]triazolo[1,5-a]azepin-2-amine; or
- (9S)-9-(3-chloro-5-fluoro-phenyl)-N-[(1S,5R,8S)-3-(6-methoxypyridazin-4-yl)-3-azabicyclo[3.2.1]octan-8-yl]-6,7,8,9-tetrahydro-5H-[1,2,4]triazolo[1,5-a]azepin-2-amine;

or a pharmaceutically acceptable acid addition salt thereof.

4. A process for preparing a compound of formula I, which process comprises:

1) reacting a compound of formula 2

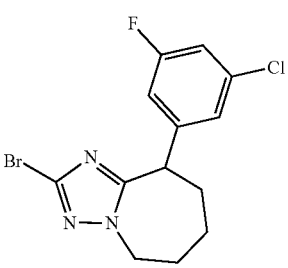

with a compound of formula 3

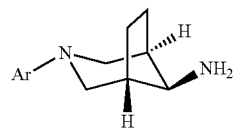

to form a compound of formula I

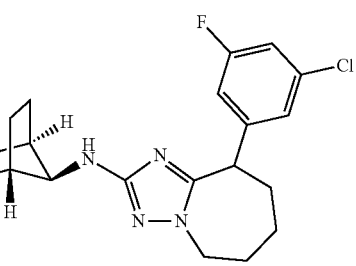

wherein Ar is

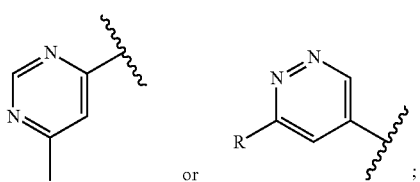

and optionally converting the compound of formula I into a pharmaceutically acceptable acid addition salt, and 2) optionally separating a racemic mixture of compounds of formula I by a chiral HPLC separation.

5. A compound prepared by a process as in claim 4.

6. A pharmaceutical preparation containing one or more compounds of claim 1 and one or more pharmaceutically acceptable excipients.

7. A method for treating Alzheimer's disease, cerebral amyloid angiopathy, hereditary cerebral hemorrhage with amyloidosis-Dutch type, multi-infarct dementia, dementia pugilistica or Down syndrome, which method comprises administering to a subject in need thereof a pharmaceutical preparation according to claim 6.

8. A method for treating of Alzheimer's disease, cerebral amyloid angiopathy, hereditary cerebral hemorrhage with amyloidosis-Dutch type, multi-infarct dementia, dementia pugilistica or Down syndrome, which method comprises administering to a subject in need thereof an effective amount of a compound as defined in claim 1.

9. The pharmaceutical preparation of claim 6 in a form selected from: tablet, coated tablet, dragée, hard gelatin capsule, soft gelatin capsule, emulsion, suspension, suppository, eye drop, and ear drop.

10. The pharmaceutical preparation of claim 6, wherein the one or more pharmaceutically acceptable excipients include one or more of:
- a preservative, solubilizer, stabilizer, wetting agent, emulsifier, sweetener, colorant, flavorant, salt, buffer, masking agent, antioxidant, and a carrier selected from lactose, corn starch, talc, stearic acid, vegetable oil, wax, glycerol, and a polyol.

11. The process of claim 4, wherein the reacting a compound of formula 2 with a compound of formula 3 is accompanied by a palladium catalyst selected from: dibromo-bis-(tritert-butyl)-phosphine palladium or tri(dibenzylideneacetone) dipalladium(0), in the presence of 2-di-tert-butylphosphino-2',4',6'-triisopropylbiphenyl and NaOt-Bu.

* * * * *